US006892583B2

(12) United States Patent
Baek

(10) Patent No.: US 6,892,583 B2
(45) Date of Patent: May 17, 2005

(54) PRESSURE SENSING DEVICE FOR RHEOMETERS

(75) Inventor: Seong-Gi Baek, Woodbury, MN (US)

(73) Assignee: Rheosense, Inc., San Ramon, CA (US)

( * ) Notice: Subject to any disclaimer, the term of this patent is extended or adjusted under 35 U.S.C. 154(b) by 35 days.

(21) Appl. No.: 10/286,602

(22) Filed: Oct. 31, 2002

(65) Prior Publication Data

US 2003/0079547 A1 May 1, 2003

Related U.S. Application Data

(60) Provisional application No. 60/335,375, filed on Oct. 31, 2001.

(51) Int. Cl.[7] ................................. G01L 7/08
(52) U.S. Cl. ..................................... 73/715
(58) Field of Search .................. 73/715, 700, 716, 73/718; 361/283.4, 283.1, 283.3

(56) References Cited

U.S. PATENT DOCUMENTS

| | | | |
|---|---|---|---|
| 4,241,602 A | | 12/1980 | Han et al. |
| 4,624,132 A | | 11/1986 | Parnaby et al. |
| 5,202,939 A | | 4/1993 | Belleville et al. |
| 5,225,959 A | | 7/1993 | Stearns |
| 5,392,117 A | | 2/1995 | Belleville et al. |
| 5,485,753 A | * | 1/1996 | Burns et al. ........... 73/720 |
| 5,663,503 A | * | 9/1997 | Dam et al. ............. 73/649 |
| 5,983,727 A | | 11/1999 | Wellman et al. |
| 6,062,088 A | | 5/2000 | Ingrisch et al. |
| 6,078,706 A | | 6/2000 | Nau et al. |
| 6,085,596 A | | 7/2000 | Jensen et al. |
| 6,725,725 B1 | * | 4/2004 | Werner et al. .......... 73/716 |

OTHER PUBLICATIONS

Dziuban, J.A. et al.; "Silicon optical pressure sensor"; Sensors and Actuators A (Physical); Apr. 1992, pp. 628–631; vol. A32, No. 1–3, Switzerland.*

Wagner, C. et al.; "Optical pressure sensor based on a Mach–Zehnder interferometer integrated with a lateral a–Si:H p–i–n photodiode"; *IEEE Photonics Technology Letters;* Oct. 1993, pp. 1257–1259; vol. 5, No. 10; USA.*

Chan M.A. et al.; "A micromachined pressure sensor with fiber–optic interferometric readout"; *Sensors and Actuators A(Physical);* May 1994, pp. 196–201; vol. A43, No. 1–3; Switzerland.*

Lee, S. B. et al.; "A micromachined interferometer for dynamic high–pressure sensing (in automotive applications)" *Sensors;* Jun. 1996, pp. 31–2, 35–6; vol. 13, No. 6; Helmers Publishing, U.S.A.*

FISO Technologies; "Product Data Sheet, FOP–M In–Vivo Pressure Sensor", 2 pages.*

FISO Technologies; "Technical Note Series, Fiber–Optic Pressure Transducer", 4 pages.*

* cited by examiner

*Primary Examiner*—Edward Lefkowitz
*Assistant Examiner*—Andre Allen
(74) *Attorney, Agent, or Firm*—Mallinckrodt & Mallinckrodt

(57) ABSTRACT

An improved rheometer plate includes a smooth sensing surface with monolithically integrated miniature pressure sensors which do not interfere with the smooth surface. Pressure sensing diaphragms formed by the smooth surface deflect in response to local pressures against the surface to enable the measurement of unperturbed local pressures of materials sheared between plates. The pressure sensors are sufficiently small that measured pressures are considered to be significantly local properties compared to the size of the plate. Normal stress differences and viscosity of fluid are measured accordingly. The membrane covers a plurality of wells or recesses with pressure sensors located in the wells to measure the deflection of the membrane over the wells. Capacitive or other sensors may be used. The rheometer plate can be used as part of a slit rheometer with a slit of varying dimensions.

26 Claims, 8 Drawing Sheets

PRESSURE SENSING DEVICE FOR RHEOMETERS

RELATED APPLICATION

Figure 1:
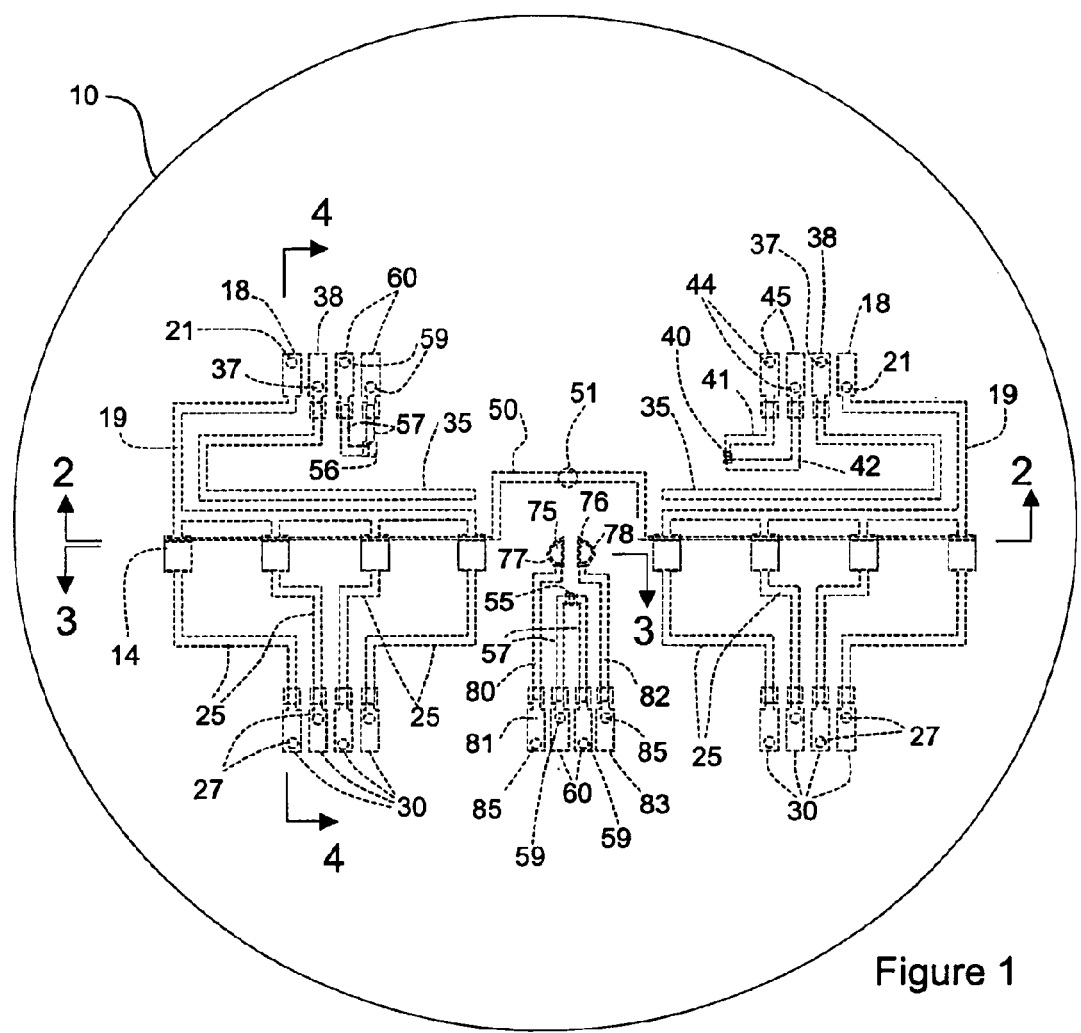

This application claims the benefit of provisional Application Ser. No. 60/335,375 filed Oct. 31, 2001, and titled "Pressure Sensing Device For Rheometers".

BACKGROUND OF THE INVENTION

1. Field

This invention is in the field of pressure measurement devices and particularly devices such as rheometer plates for measuring local pressures of fluids during shear and restricted flow.

2. State of the Art

Normal stress differences and viscosities are important properties of plastics and other liquids that need to be characterized and taken into account for the efficient processing of these liquids. One way to measure normal stress differences is to measure the local pressure of the fluid under shear conditions against a rheometer plate. Fluid is sheared between one stationary plate and a rotating cone or plate. The stationary plate is connected to a spring, which deflects in response to the normal stress difference of the liquid being sheared. However, with this method, the deflection of the spring results in a change of the gap between the stationary plate and the rotating cone. For accurate measurement, this gap should be held constant during measurement. In order to minimize the change in the gap, a substantially stiff spring has been employed. The stiff spring, however, requires a very elaborate detection circuit for accurate detection of small deflection. A servo system may be employed to compensate for the deflection automatically. However, the finite response time of the feedback control of the servo system is a source of uncertainty especially under a dynamic control system. The accuracy of the detection circuit sets up a limit on minimum size of the rheometer plate, which determines the amount of deflection of the spring. In other words, the accuracy of the normal stress difference measurement depends on the size of the plate and the detection circuit accuracy.

Alternatively, rather than using a spring mounted rheometer plate and measuring the displacement of the plate under pressure of the liquid against the plate, a fixed rheometer plate with two or more pressure sensors attached to the plate can be used to measure pressure exerted by the liquid during shear at the locations on the plate where the pressure sensors are located. This alternative method is described in Ramachandran, S. and E. B. Chriatiansen, AIChe 1985, 31, 162; Seong-Gi Baek, Ph.D. Thesis, University of Utah, 1991; and S. G. Baek, J, J, Magda, S. Cementwala, J. of Rheology, 1993, 37 (5), 935. As described in these references, individual pressure transducers are mounted to a stationary plate. The sensing diaphragms of individual pressure transducers, however, should be flush mounted with the stationary surface in order not to disturb flow due to the roughness generated otherwise. Thus, the mounting of the individual transducers has to be done carefully to minimize surface roughness. However, it is generally impossible to remove such surface roughness completely with sensors individually mounted in the surface, so some effect from the roughness will always be present.

With the type of rheometer described above, setting the right distance between the cone and the plate and keeping it during measurement is critical for accuracy. With current rheometers, the distance is set mechanically. First the cone is lowered until it touches the plate. Then the cone is raised to the specified distance from the point of contact for a gap. Current rheometers, however, do not provide any mean to monitor the position of the cone during measurement.

Rather than using a rheometer plate with a rotating cone creating the shear in the liquid to be measured, the liquid can be forced through a flow passage and the pressure exerted on the walls of the passage measured similarly to the pressure on the rheometer plate. Generally, the liquid will be forced through a passage having set dimensions and the pressure exerted against a wall of the passage will be measured by pressure transducers set in the wall. Again, it is important to keep the wall as smooth as possible. Using a flow passage with set dimensions can provide a measurement of the apparent viscosity of the liquid. If the liquid is then forced through a second device with a flow passage of different set dimensions, the pressure measurements obtained can be compared to the first measurements and the exact viscosity calculated.

U.S. Pat. No. 5,983,727 shows a device for measuring the pressure of liquids against a surface of the device. The device has a mounting structure with a recess therein. An elastic membrane extends over the recess and at least one transducer is mounted in the recess to detect deflection of the membrane at a selected plurality of regions on the membrane. However, relatively complex sensors are required to measure deflection at a plurality of regions on the membrane or to separate measurements made by several sensors in the same recess measuring different regions of the membrane.

SUMMARY OF THE INVENTION

According to the invention, surface roughness on a rheometer plate can be substantially eliminated by providing a rheometer plate with monolithically integrated pressure transducers. The plate forms a single substantially smooth surface against which the liquid generating the pressure to be measured acts. With such arrangement, accuracy of normal stress difference measurement depends only on transducer resolution, not on the size of plate. This also allows the employment of a smaller plate for normal stress difference measurements. With a smaller plate, higher shear rates can be accessed due to a deterred onset of flow instability by smaller centrifugal force and a lower tendency to fracture. Also, a smaller amount of sample is required.

Advances in microfabrication and micromachining processes enable the miniaturization of sensitive solid-state capacitive pressure transducers and read-out circuits. Capacitive type pressure transducers can be tailored to have a wide range of sensitivity by changing dimensions (gap, sizes) of the capacitor and rigidity of the deflecting membrane. Read out circuits are critical components and there are three approaches for capacitance measurement: capacitance bridges as described in J. M. McCreary and D. A. Sealer, Precision Capacitor Measurement Techniques for Integrated Circuit Capacitor Arrays, IEEE Trans. Instrum. And Meas., Vol. IM-28, pp. 11–17, March, 1979, and Watanabe and G. C. Temes, Switched-Capacitor Digital Capacitance Bridge, IEEE Trans. Instrum. and Meas., Vol. IM-33, pp. 247–251, December, 1984; relaxation oscillators as described in F. Krummenacher, High Resolution Capacitance To Frequency Converter, IEEE Journal of Solid State Circuits, Vol. SC-20, No. 3, June, 1985, and M. Smith, L. Bowman, and J. Meindl, Analysis, Design and Performance of a Capacitive Pressure Sensor IC, IEEE Trans. On Biomedical Eng., Vol. BME-33, No. 2, pp. 163–174, February, 1986; and switched capacitors as described in G. J. Yeh, I. Dendo, and W. H. Ko, Switched Capacitor Interface Circuit for Capacitive Transducers, Transducers 5, pp. 60–63, June, 1985. The cited references are hereby incorporated by reference.

In a preferred embodiment of the invention, the rheometer plate includes a plurality of cavities formed therein so that the smooth measuring surface of the plate extends over the cavities to form an end of the cavity which will deform slightly in response to pressure applied to the smooth surface over the cavity. A single, simple capacitive pressure sensor is formed in each cavity to provide a measurement of the deflection of the end of the cavity and thus a measurement of the pressure applied by the liquid under test against the surface over the cavity. The cavities, and thus the pressure sensors, are located as desired over the plate with such locations and number of cavities chosen to provide desired measurements for the particular tests to be performed using the plate. The plate may be formed of two or more layers of material secured together and fabricated to form the desired cavities and sensors.

A preferred fabrication method of the invention is either surface micromachining or bulk micromachining, or a combination of these. A preferred method using bulk micromachining is to use a plate or membrane of elastic material. In the preferred method, at least two wells are formed in the plate or membrane by chemical etching or plasma etching or the combination of these. The membrane with wells is further combined with a substrate so that the wells create the cavities in the plate. Capacitive pressure sensors are formed in each cavity. The membrane is further thinned down by chemical etching, plasma etching, chemical or mechanical polishing (CMP), or a combination of these to tailor the sensitivity of the sensor, if desired. With surface micromachining, each pressure sensor is constructed directly on a substrate. In this case, however, planarization is necessary to ensure a sufficient smoothness of the liquid contacting side of the plate.

Another preferred method is to form at least two wells on the bottom substrate by chemical etching, plasma etching, or a combination of these. The substrate is further combined with a flat top plate or membrane so that the wells create the cavities in the plate. Capacitive transducers are formed in each cavity. After the combination, the plate is further thinned down by chemical etching, plasma etching, electrochemical etching, chemical or mechanical polishing (CMP), or a combination of these to tailor the sensitivity.

A preferred method using surface micromachining is to form at least two wells on the substrate. Each well has a conductor and the conductor forms the bottom half of the capacitor. The top half of the capacitor is made by depositing a conductor on top of the bottom half of the capacitor with a sacrificial layer in between. The sacrificial layer is further removed by chemical etching or plasma etching to create the cavities. Then the substrate is further coated uniformly for planarization.

The rheometer plate of the invention may be used as the stationary plate in conjunction with a rotating cone for generating the shear to be measured or may be used as a wall of a passage in a slit rheometer device. In addition, the invention also includes a novel miniature slit rheometer device having a slit or flow passage with a plurality of steps to provide varying dimensions so that exact viscosity can be measured using a single device rather than having to switch between two or more devices.

The rheometer plate can include a proximity or distance sensor to electronically detect the position of the cone with respect to the plate so that the point of contact does not need to be measured separately. Such sensor can further continuously monitor the position of the cone during measurement, which will improve greatly the accuracy of measurement.

The primary object of present invention is to provide a rheometer plate with pressure sensors integrated monolithically in order to eliminate the step of mounting individual pressure transducers or a strip of pressure transducers as is necessary in past practice. This provides a smooth surfaced plate that does not affect the pressure exerted by the liquid against the plate. Furthermore, the miniaturization of the pressure measuring sensors allows the miniaturization of the rheometer plate. On-chip or near on-chip read-out circuits, analog to digital converters (ADC), input/output interfaces (I/O) for communication with a host process controller, and, if desired, telemetry circuits for wireless communication with a host process controller, may be provided to enhance the measurement accuracy by minimizing the noise to signal ratio. Temperature sensors may be included in the rheometer plate to measure temperature changes, and multiple temperature sensors can be arranged to measure temperature gradients along the plate. In addition, a proximity sensor may be included in the rheometer plate to detect and continuously monitor the gap between the rheometer plate and the cone. Additional on-chip data analysis circuits and systems may also be provided.

THE DRAWINGS

Figure 2:
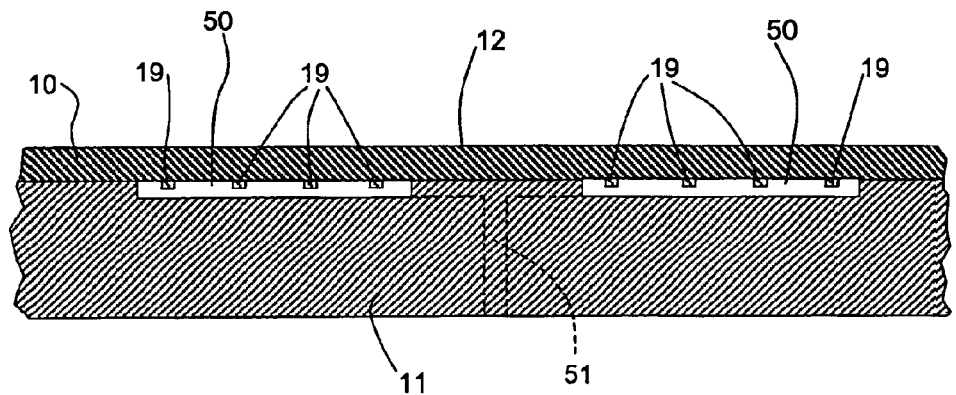
Figure 3:
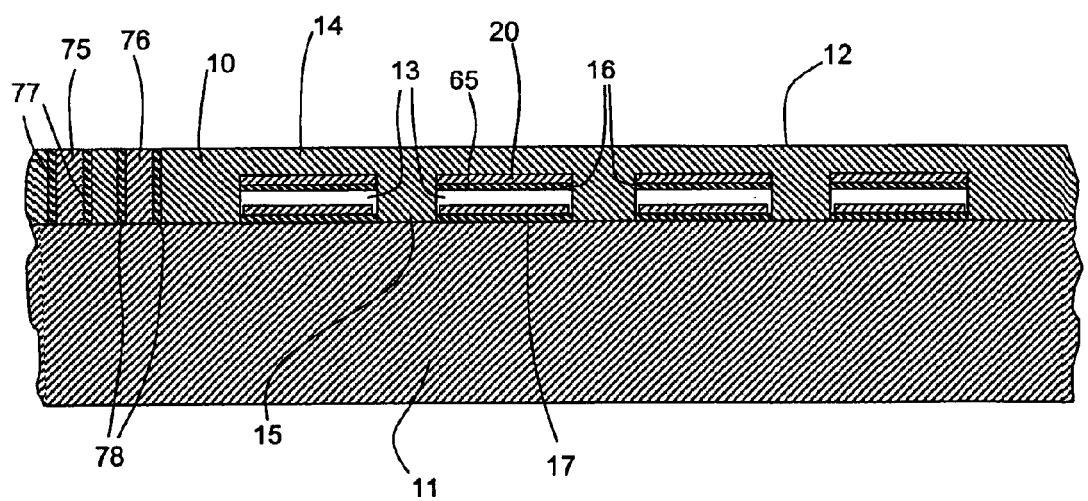
Figure 4:
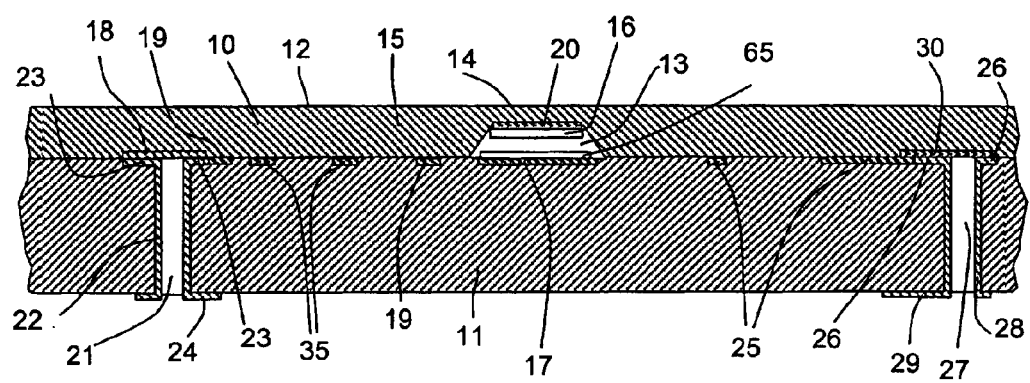
Figure 5:
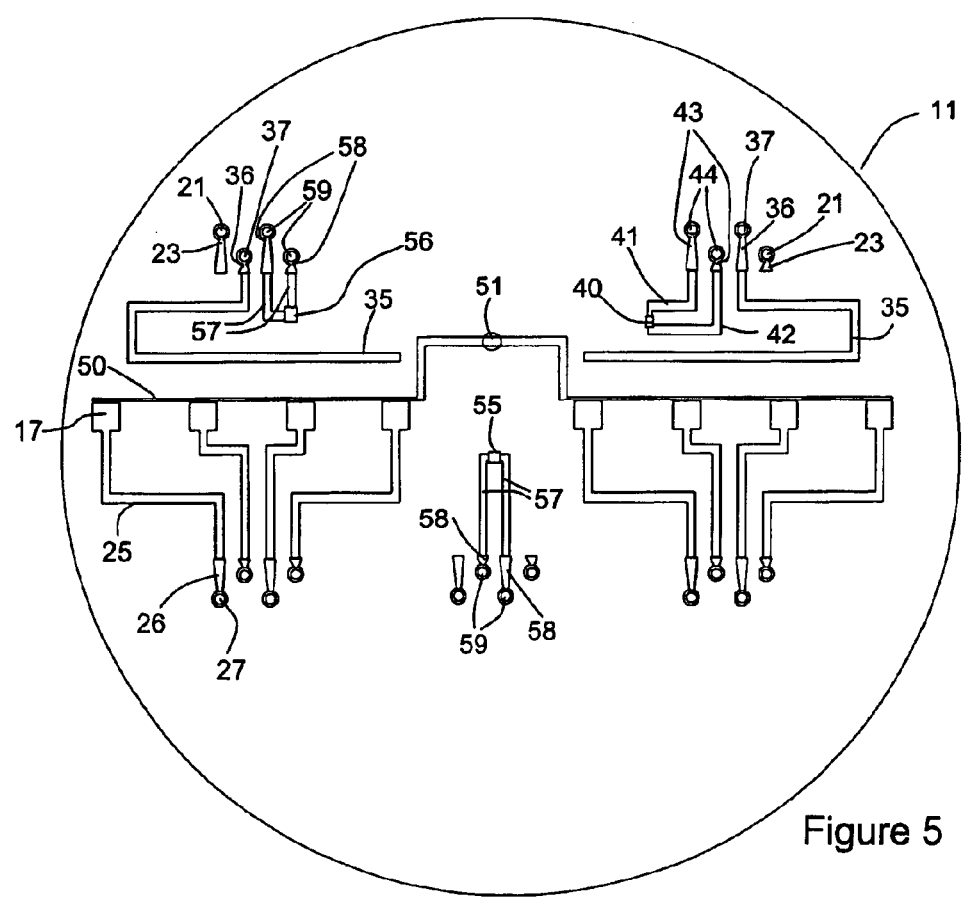
Figure 6:
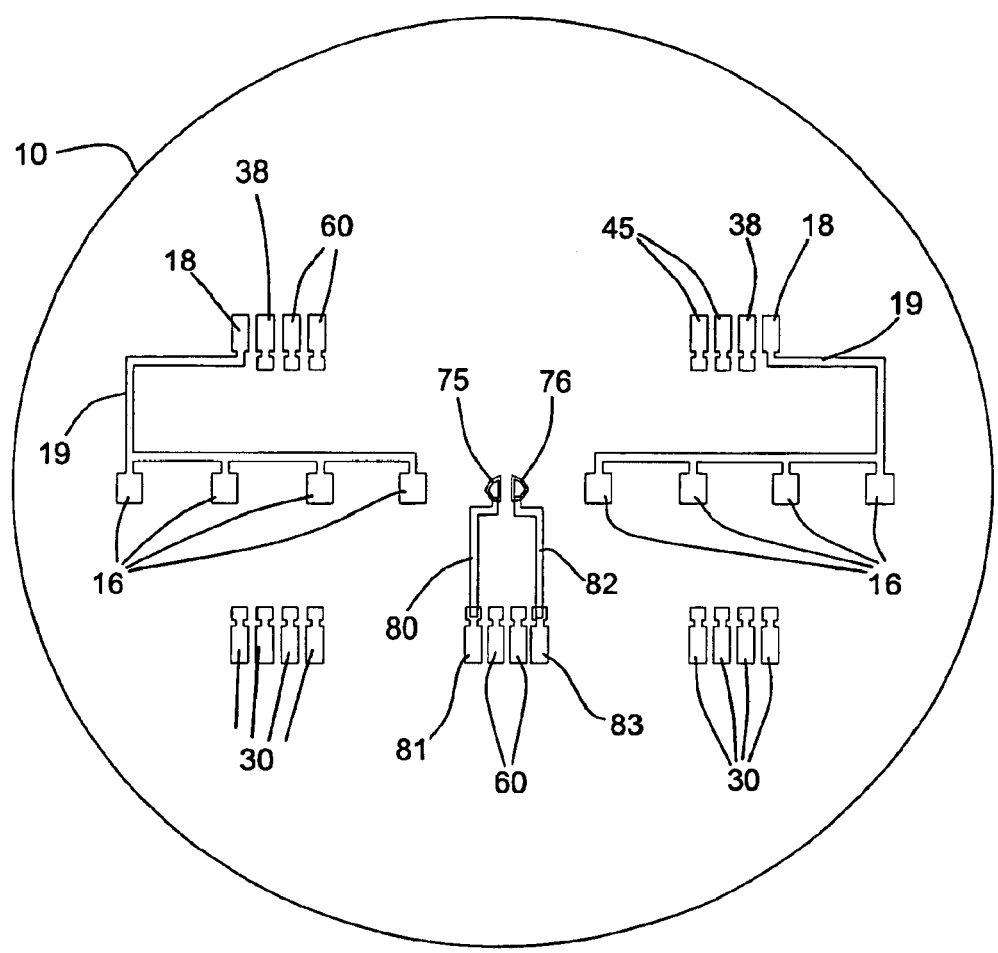
Figure 7:
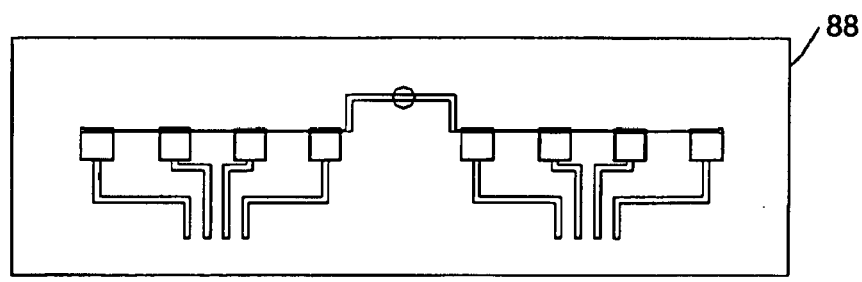
Figure 8:
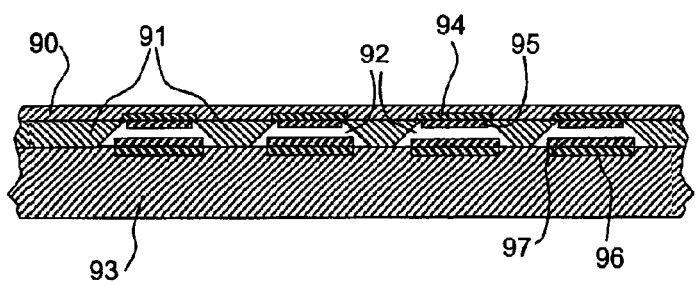
Figure 9:
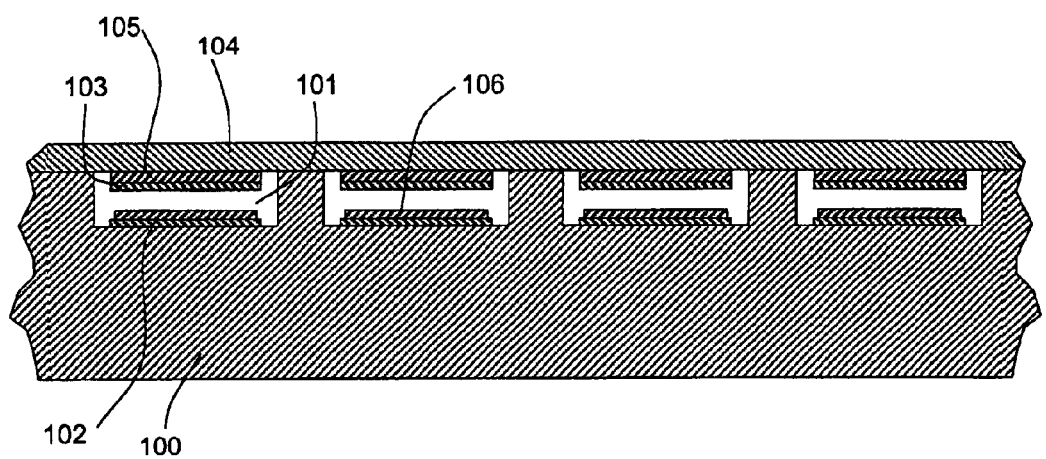
Figure 10:
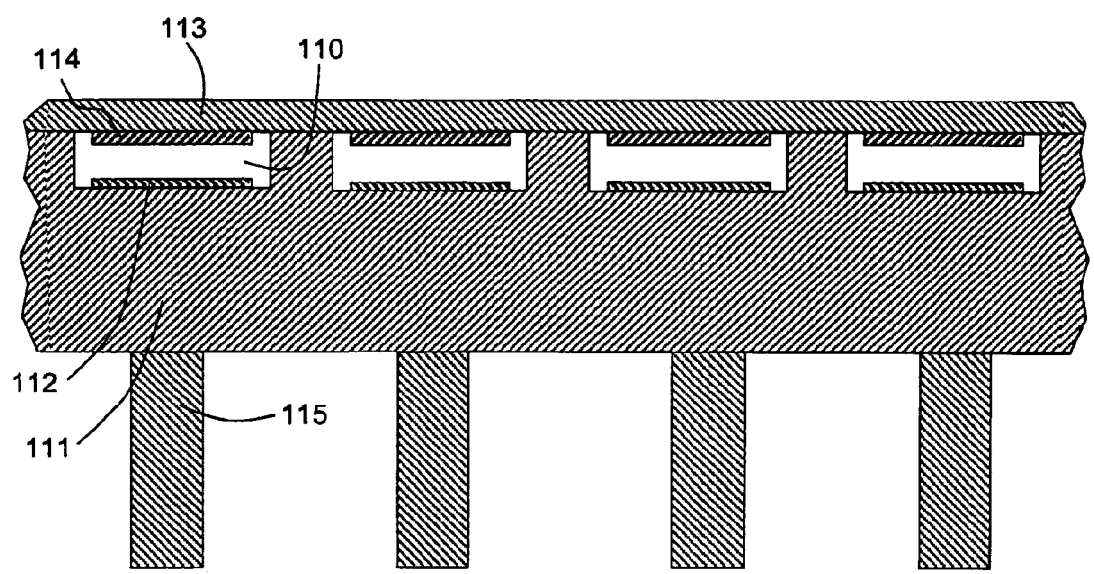
Figure 11:
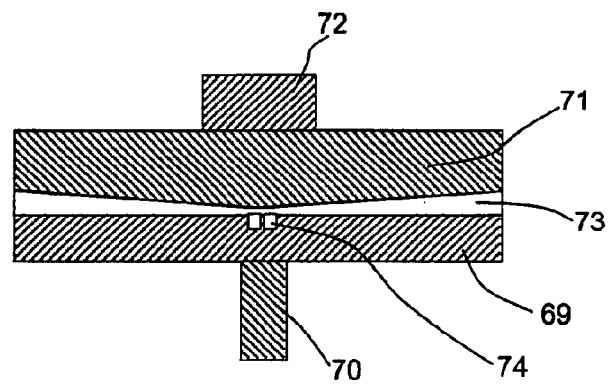
Figure 12:
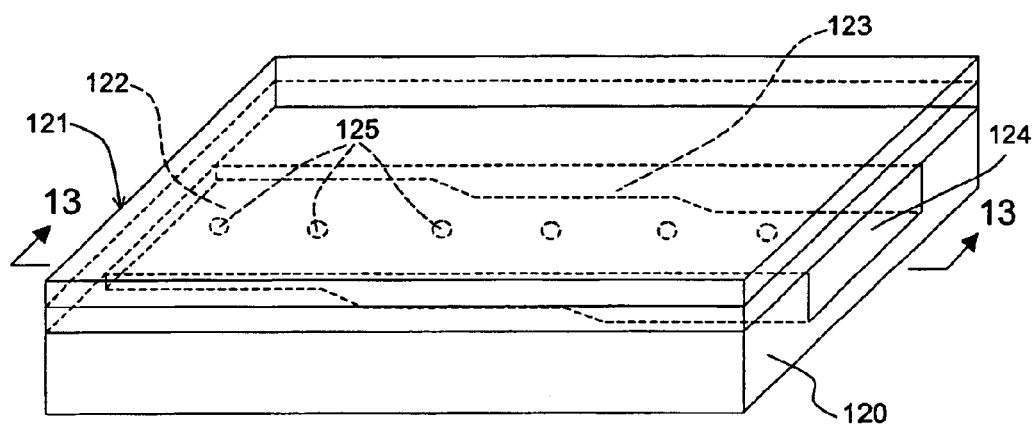
Figure 13:
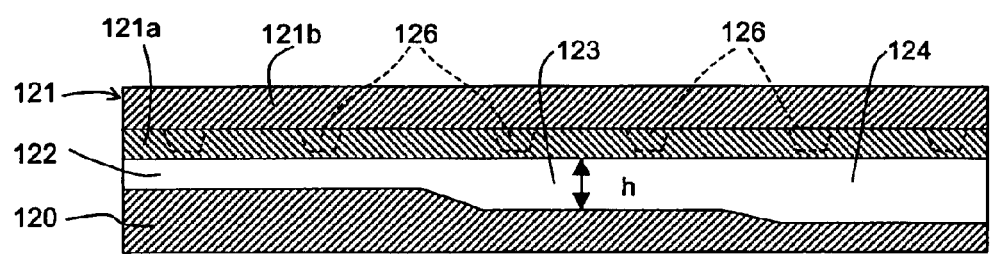
Figure 14:
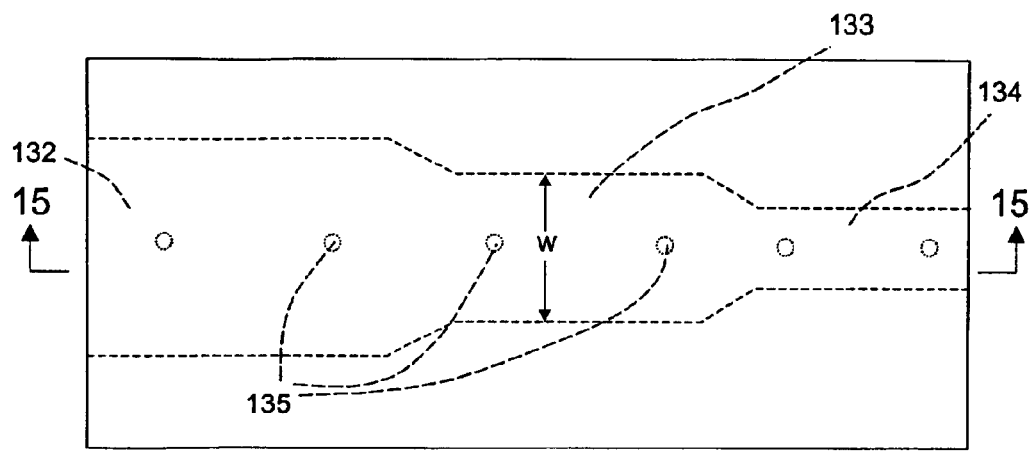

The best mode presently contemplated for carrying out the invention is illustrated in the accompany drawings, in which:

FIG. 1 is a top plan view of an assembled rheometer plate of the invention, the smooth liquid contacting surface of the plate arbitrarily being considered as the top surface, and showing various internal components of the assembled rheometer plate as if the plate were transparent;

FIG. 2, a fragmentary vertical section taken on the line 2—2 of FIG. 1;

FIG. 3, a fragmentary vertical section taken on the line 3—3 of FIG. 1;

FIG. 4, a fragmentary vertical section taken on the line 4—4 of FIG. 1;

FIG. 5, a top plan view of the bottom wafer or substrate of the rheometer plate of FIG. 1;

FIG. 6, a bottom plan view of the top wafer or membrane of the rheometer plate of FIG. 1;

FIG. 7, a top plan view similar to that of FIG. 1, but showing an alternative design of the rheometer plate;

FIG. 8, a fragmentary vertical section similar to the vertical section of FIG. 2, but showing a different embodiment of sensor construction;

FIG. 9, a fragmentary vertical section similar to the vertical section of FIG. 2, but showing a different embodiment of plate construction;

FIG. 10, a fragmentary vertical section similar to the vertical section of FIG. 2, but showing a different embodiment of sensor construction;

FIG. 11, a schematic side elevation of a rheometer using a rheometer plate of the invention, and showing how a rheometer plate of the invention may be used with a cone spaced from the rheometer plate, and a sample to be tested between the cone and rheometer plate;

FIG. 12, a perspective view of a slit rheometer with a rheometer plate of the invention as a part thereof;

FIG. 13, a vertical section of the slit rheometer of FIG. 12;

FIG. 14, a top plan view of a different embodiment of slit rheometer; and

Figure 15:
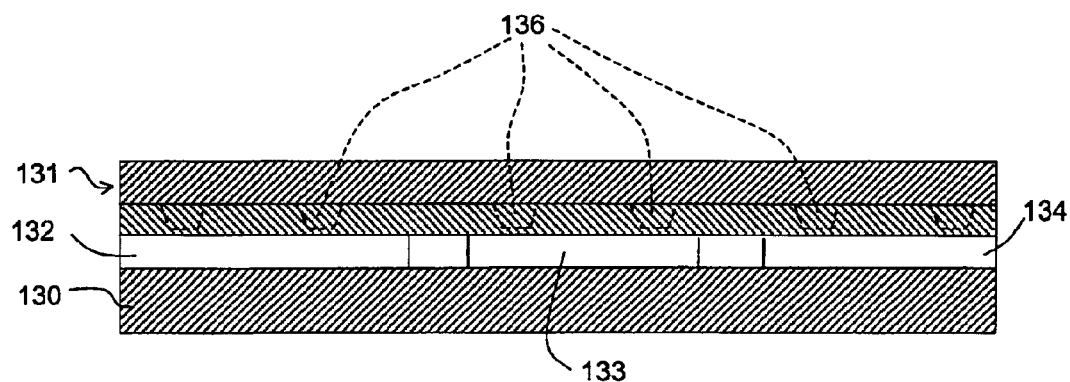

FIG. 15, a vertical section of the slit rheometer of FIG. 14.

DETAILED DESCRIPTION OF THE ILLUSTRATED EMBODIMENT

In order to measure the local pressure of a liquid under well-defined unperturbed states for measuring accurate normal stress differences, it is desirable to have a smooth rheometer plate against which the liquid acts and which has a plurality of pressure sensors spaced in the plate to measure pressure at the locations of the pressure sensors. To provide a smooth surface against which the liquid can act, a rheometer plate according to the invention is constructed using a membrane, such as formed by a silicon wafer, to maintain the smooth surface of the plate, and includes monolithically integrated pressure sensors. Various types of pressure sensors may be used, such as capacitive pressure sensors. An embiodment of the rheometer plate of the invention with capacitive pressure sensors is shown in FIGS. 1–6. The monolithically constructed plate comprises a top wafer or membrane 10, FIGS. 2, 3, and 4, and a bottom wafer or substrate 11. The top membrane 10 is preferably a silicon wafer having a smooth top surface 12 and processed to form a plurality of wells or recesses 13 in the underside thereof, which provide thin, elastic sections 14 of the top membrane material over the wells or recesses 13, with thick supporting sections 15 therebetween. Various materials other than silicon that can be etched to form wells in a controlled manner with chemical etchant or plasma etchant or the combination of both may be used for the top wafer, such as gallium arsenide. Depending upon the liquid being measured, it may be desirable to coat the top smooth surface 12 with a material to resist chemical or physical interaction between the liquid and the surface and/or to resist abrasion of the surface by the liquid. The bottom wafer 11 may be made of a glass material such as a Corning Pyrex wafer #7740 or a BOROFLOAT wafer from Schott Corporation. The material forming the bottom wafer should be sufficiently rigid to be used as a substrate in semiconductor or Microelectromechanical systems (MEMS).

The thin sections 14 are elastic enough to deflect or deform slightly in response to local unpreturbed pressures against the smooth surface 12 of the thin sections 14 of top wafer 10. In order to detect and measure the deflection or deformation of thin sections 14, a capacitor is formed in each recess or well 13 by capacitor plate 16 mounted on the thin section 14 inside recess 13 in association with another capacitor plate 17 mounted on bottom glass wafer 11 at the opposite end of recess 13 when the top and bottom wafers are joined. When the wafers are joined, the wells create cavities in the plate formed by the joined wafers. Changes in the deflection of thin section 14 change the distance between the capacitor plates 16 and 17 thereby changing the capacitance of the capacitor formed by the capacitor plates. By measuring the capacitance and changes in capacitance of each of these capacitors, the deflection of the respective measuring surface of the thin sections 14 is determined. From that, the pressure applied by the liquid to the respective thin sections 14 is determined since the deflection is caused by and is porpotional to the pressure applied to the thin sections by the liquid.

The wells 13 in the top wafer 10 may be made using a photolithography process followed by wet chemical etching or dry plasma etching or the combination of these to form the recesses or wells 13. Once the wells are formed, conductive films forming the plates 16 of the capacitors, contact pads 18, and leads 19 extending from the respective capacitor plates 16 to connect with respective contact pads 18, FIGS. 1, 3, 4, and 6, are deposited on the under surface of top wafer 10. A dielectric layer 20, FIGS. 3 and 4, may be formed for insulation purposes between thin sections 14 and capacitor plates 16, when desired. It should be noted that dielectric layer 20 is formed on thin sections 14 of top wafer 10 prior to deposition of capacitor plates 16. Further, although not shown, it is preferred to form dielectric layer 20 to cover the entire underside of top wafer 10 to isolate the silicon of the wafer from the various leads and other components deposited on the underside of the top wafer. In the embodiment of FIGS. 1–6, sets of four capacitor plates 16 are all connected in parallel by respective leads 19 to respective contact pads 18, FIGS. 1 and 6.

In order to connect the capacitor plates 16 to measurement circuitry, connection holes 21 are provided through bottom wafer 11, FIG. 4. Wire leads may be connected in known manner to contact pads 18 and pass through appropriate holes 21 to outside circuitry, but preferably, as shown, holes 21 are plated with a conductive material 22 which forms a contact 23 on the inside surface of bottom wafer 11 which makes electrical contact with contact pads 18 of the top wafer when the two are joined. The plating also forms electrical contact pads 24 on the bottom of bottom wafer 11 to which wires or other leads may be connected to connect to desired circuitry. In manufacture of the rheometer plates, disposition of the conductive material 22 and contacts 23 on the inside surface of bottom wafer 11 will be done prior to joining the top and bottom wafers, with additional deposition of conductive material, such as by sputtering, done after joining of the wafers to deposit additional conductive material in holes 21 and onto contact pads 18 to ensure a good electrical connection to contact pads 18 and to form contact pads 24 on the bottom of bottom wafer 11.

Conductive films forming capacitor plates 17 on bottom wafer 11, along with leads 25 extending from respective capacitor plates 17, are deposited on the inner surface of bottom wafer 11. Leads 25 connect with inner contacts 26 of holes 27, similar to holes 21. Holes 27 have inside conductive material 28 and outside contact pads 29. Each of the capacitor plates 17 is connected separately by a lead 25 to a separate hole 27, FIGS. 1 and 5. Contact pads 30 may also be provided on top wafer 10 located to make electrical contact with ends of leads 25 and contacts 26 to ensure good electrical contact between them.

Electrical grounding conductors 35 extend from inner contact 36 of holes 37, similar to holes 21. Contact pads 38 may also be provided on top wafer 10 located to make electrical contact with ends of conductors 35 and contacts 36 to ensure good electrical contact between them. Presence of the grounding conductors reduce electrical noise in the device.

It is also generally desirable to provide a reference capacitor 40 with leads 41 and 42 connecting to respective contacts 43 of respective holes 44. Reference capacitor 40 will be constructed with a pair of capacitor plates with a dielectric layer therebetween deposited on one of the plates, here shown as on the inside surface of the bottom plate 11. Alternately, a portion of the reference capacitor could be deposited on the inside surface of the bottom wafer with other portions on the underside of the top wafer. Contact pads 45 may also be provided on top wafer 10 located to make electrical contact with ends of leads 41 and 42 and respective contacts 43 to ensure good electrical contact between them. The capacitance of the reference capacitor is not subject to change with fluid pressure changes, but is subject to the same temperature changes as the capacitive sensors so acts as a reference for capacitive changes due to temperature changes in the device.

To prevent a change in pressure in the recesses or wells 13 with movement of the thin portion 14, bottom glass wafer 11 may include an air passage 50, FIGS. 1, 2, and 5, connecting all wells 13 to an air hole 51 connecting to the atmosphere.

The viscosity of a liquid generally varies with the temperature of the liquid. In many instances, the sample liquid tested is at an elevated temperature and different temperatures may be present in different portions of the sample. Thus, increased accuracy of the measurements may be obtained by measuring the temperature of the rheometer plate and any temperature gradients in the plate. The temperature of the plate generally represents the temperature of the sample in contact with the plate at the location of the temperature sensor. Various types of temperature sensors may be used such as thermocouples, thermisters, transistors, etc., which can be formed by a deposit of polysilicon on one of the wafers 10 or 11. Alternately, as indicated, a capacitor similar to reference capacitor 40 can serve as a temperature sensor since the capacitance will change with temperature change. For example, temperature sensors 55 and 56 may be formed on the inner surface of bottom wafer 11 with leads 57 connecting opposite sides of temperature sensors 55 and 56 to contacts 58 of holes 59, FIGS. 1 and 5. Contact pads 60, FIGS. 1 and 6, may also be provided on top wafer 10 located to make electrical contact with ends of leads 57 and contacts 58 to ensure good electrical contact between them. Usually, one of these temperature sensors, here sensor 55, will be located toward the center of the rheometer plate with the other temperature sensor or sensors arranged radially outwardly from the center so that any radial temperature gradient that may exist can be detected and measured.

As indicated, the various capacitor plates, conductive leads, contact pads, insulating layers, etc., are deposited on either the undersurface of the top wafer 10 or the inner surface of the bottom wafer 11. Once the various layers are deposited, the top wafer 10 and bottom wafer 11 are joined, such as electro statically, with low temperature glass bonding methods, with eutectic bonding methods, or with other methods commonly used in microelectromechanical systems. An oxide film 65 may be deposited on capacitor plate 16 and/or capacitor plate 17, if desired, to provide an insulating layer between plates 16 and 17 to prevent direct contact and shorting out under excessive pressure. A similar oxide insulating layer can be deposited on other components to insulate such components on one wafer from those on the other wafer when the wafers are joined.

One principal use of the rheometer plate of the invention is in a rheometer having a stationary plate and a rotating cone. Such a rheometer is shown schematically in FIG. 11. The stationary rheometer plate 69 is a circular plate of the invention with pressure sensors distributed over the plate as shown in FIG. 1, supported by a base 70. A rotatable cone 71 is support by a shaft 72 connected to a motor or other means for causing rotation of the cone. The cone 71 is also mounted so that it can be raised and lowered with respect to plate 70. A sample 73 is positioned between cone 71 and stationary plate 69. During the test, cone 71 is rotated while measurements of pressure are taken from the pressure sensors in the stationary plate 69. With this type of rheometer, setting the right distance between the cone and the plate and keeping it during measurement is critical for accuracy. With current rheometers of this type, the cone is first lowered until it touches the plate. The cone is then raised to the specified distance from the point of contact to create the desired gap. It has been found that with the rheometer plate of the invention, a proximity sensor 74 can be included in the plate, preferably in the center of the plate to measure the distance of the cone from the plate. In this way, the cone can be easily and accurately set the desired distance from the plate. Further, the distance can be monitored and the position of cone 71 continuously adjusted to maintain it at the desired distance from the plate for more accurate measurements than can be currently obtained.

Various types of proximity sensors can be built into the rheometer plate of the invention and used to measure the distance. It has been found that a capacitive sensor can be used, however, it must be arranged differently than the capacitive pressure sensors described. Further, it is preferred that the sensor be arranged centrally of the rheometer plate. As shown in FIGS. 1 and 3, top wafer 10 is treated to form two conductors 75 and 76 electrically isolated from the remainder of the wafer by an insulating layer 77 surrounding conductor 75 and an insulating layer 78 surrounding conductor 76. These conductors form the two plates of a capacitor arranged perpendicularly to the plates of the pressure sensor capacitors in wafer 10. As viewed from the orientation of FIG. 3, the conductors extend vertically through top wafer 10. The capacitance will change proportionally with the distance of the cone from the plate. Lead 80 connects conductor 75 to contact pad 81, while lead 82 connects conductor 76 to contact pad 83. Contact pads 81 and 83 contact and electrically connect to contacts 84 and holes 85 when the top and bottom wafers are joined.

While various materials may be used in the invention and various sizes may be used, the top wafer should be at least about twelve microns thick so that the top thin section can be at least about seven microns thick and the wells can be at least about five microns deep. The top thin section, when made of silicon, may range from about seven microns to about 300 microns in thickness and the wells may range from about five microns to about 300 microns in depth. When a glass wafer is used for the bottom wafer, the bottom should be at least about of a millimeter thick to provide rigidity to the assembled plate. Of course, the dimensions will depend upon the materials used and the particular construction used, the critical factors being that the thin areas have enough elasticity to deform under expected pressures to be measured, that the wells be dimensioned to provide room for the sensor configuration or sensors used, and that together, the assembled rheometer plate have the desired rigidity and sensitivity for the particular application contemplated in a particular situation. If the thickness of the stating top wafer is thicker than desired, the top wafer is preferably thinned down to the desired thickness by wet chemical etching, dry plasma etching, chemical or mechanical polishing, or the combination of these methods after the top and the bottom wafers are combined together. The size of each capacitive pressure transducer is preferably less than one quarter of the length of the plate. Also, the plate itself may vary in size. A satisfactory plate for use in a rheometer as shown in FIG. 11 is a round plate about one inch in diameter, although plates up to about four inches could be used.

As an example, a silicon-on-insulator (SOI) wafer was used to form the top wafer 10. The example SOI consisted of 400 $\mu$m thick handle silicon, 12 $\mu$m thick device silicon, and a 2 $\mu$m thick buried oxide layer between the silicons. The wells 12 were formed on the device silicon using photolithography and etching in sequence. After metals were deposited and patterned in a known manner on the device silicon, the SOI was bonded electrostatically to the processed Pyrex 7740 wafer. The handle silicon and the oxide layer were then etched away. The involved processes for the top wafer can be varied depending on the type of silicon wafers used. Another example is to use a silicon wafer with epitaxially grown heavily doped $p^{++}$ silicon. The $p^{++}$ silicon is etched with $SF_6/C_4F_8$ plasma etcher to form the wells. Then the wafer is bonded to the processed pyrex wafer. The excess silicon is then removed with KOH solution or ethylene diamine pyrochatechol (EDP) solution. Alternatively, a p type silicon wafer with epitaxially grown thin n type silicon on top is used to make the top wafer. The n-type silicon is etched to form wells and then is bonded to the processed pyrex wafer. The excess p type silicon is later etched away with electrochemical etching.

When an SOI wafer is used for the top wafer, the two conductors of the capacitive proximity sensor are formed as conductive cores in the device silicon of the SOI. The conductive cores are electrically separated from the device silicon by oxide layers formed between the conductive cores and the device silicon. The conductive core may be a highly doped polysilicon.

The sensitivities and measurable pressure range of the sensors or transducers may be uniform in a particular plate, or may be tailored in any desired way. For example, the sensors closer to one end or side of the plate may be made more sensitive than those closer to the other end, or, with circular plates, the sensors in the center of the plate can be more sensitive or less sensitive than those toward the outside of the plate. The sensors can change progressively moving from center to outside or from one side to the other. The sensitivities of the sensors may be changed by changing the thickness of the deformable thin sections, by changing the size of the wells thereby enlarging or reducing the size of the thin sections, or by other appropriate methods. Employing sensors with different sensitivity and measurable full scale pressure on a single plate is a very efficient way to increase the extent of the accessible test conditions if pressure ranges are not uniform.

The rheometer plate when used in a rheometer such as shown in FIG. 11 is preferably circular in shape. However, the plate may be rectangular, and in various applications, a rectangular plate, as shown in FIG. 7, is preferred. FIG. 7, shows the inside surface of a bottom wafer 88 and will be similar-in construction to bottom wafer 11 of FIG. 5. The top wafer will be of the same rectangular shape and be similar in construction to top wafer 10 of FIG. 6. Such wafers may include all features of the wafers of FIGS. 5 and 6 although not specifically shown. These are therefore not described in further detail. Again, the size of the pressure sensors are preferably less than one quarter of the longer length of the plate.

Rather than forming wells in a single top wafer so that the thin sections and the supporting sections of the top wafer are formed as a single piece, a two piece top wafer may be formed from a substantially flat wafer 90 and a spacer wafer 91 having openings 92 therethrough to space the flat wafer 90 from bottom wafer 93 and form wells corresponding with the openings 92 in spacer 91. This will make substantially the same rheometer plate configuration as that shown in FIGS. 1–6. The flat wafer 90 can be a silicon wafer, with the bottom wafer 93 of glass as described for FIGS. 1–6. The spacer 91 may be of silicon, glass, or other material that will provide the desired support to flat wafer 90. The spacer can be materials deposited on either flat wafer 90 or bottom wafer 93 by chemical vapor deposition (CVD) methods, evaporation methods, sputtering method, or a combination of these methods. Insulating layer 94 with capacitor plate 95 are deposited on flat wafer 90 while capacitor plate 96 and insulating oxide layer 97 are deposited on bottom wafer 93. Connections of the capacitor plates and other features will be similar to those shown in FIGS. 1–6.

Rather than forming wells in the top wafer as shown in FIGS. 1–6, or providing a spacer as shown in FIG. 8, the bottom wafer 100, FIG. 9 can be processed with wet chemical etching or dry plasma etching or a combination of these to form wells 101 in the bottom wafer. A capacitor is formed by depositing capacitor plate 102 in wells 101 in bottom wafer 100 and the other capacitor plate 103 is deposited on top wafer 104, preferably with an insulating layer 105 therebetween. Top wafer 104 is uniform in thickness across the plate and the surface in direct contact with liquid is sufficiently smooth. Top wafer 104 is bonded to bottom wafer 100. An oxide film or other insulating film 106 may be deposited to prevent shorting or to provide insulation. The top wafer 104 is preferably thinned down to the desired thickness by chemical or mechanical polishing, wet chemical etching, dry plasma etching, electrochemical etching, or a combination of these methods after the thicker top wafer and the bottom wafer are bonded together. Connections of the capacitor plates and other features will be similar to those shown in FIGS. 1–6.

While it is currently preferred that the various circuits and circuit components such as the read-out circuits, signal generators, ADC circuits, I/O controllers, temperature sensors, and/or telemetry circuits be built into or be built onto one of the wafers, such circuits can be separately mounted on a wafer or can be separate from the wafers with conductors extending from the wafers to such circuits. As described for FIGS. 1–6, the various capacitor plates, reference capacitor, ground conductor, temperature sensors, and proximity sensor conductors are all electrically connected through holes in bottom wafer 11 to contact pads formed on the bottom of bottom wafer 11. These contact pads are easily accessible to a user. Wires are easily connected to these contact pads, such as by soldering, and can connect the various components on the wafers to various desired circuits. The various circuits mentioned and the various circuits needed to process the signals from the sensors on the plate are all well known and are not described further.

As indicated, while capacitive pressure sensors have been illustrated in relation to the embodiments described so far, various other types of pressure sensors can be used. For example, optical sensors such as Fabry-Perot Interferometer pressure sensors can be used instead of the capacitive pressure sensors as shown in FIG. 10. Each capacitive pressure sensor described above is replaced by a Fabry-Perot optical pressure sensor. Optical cavities 110 are formed in glass bottom wafer or substrate 111 by etching such cavities followed by the deposition of a partially transparent layer 112 in the bottom of the cavities. Top wafer or membrane 113 has reflective mirrors 114 deposited thereon at the other end of the cavities. The top membrane and the glass substrate are electrostatically bonded (anodic bonding) together. Optical fibers 115, are mounted in the substrate to direct light to the partially transparent layer 112. Part of the light passes through the partially transparent layer 112 into a cavity 110 and toward reflective mirror 114, while part of the light is reflected back from the partially transparent layer 112 to the optical fiber. The light that passes through the partially transparent layer is reflected back by mirror 114 and the reflected light passes through the partially transparent layer and sets up an interference pattern with the light reflected directly from the partially transparent layer. This light from the interference pattern is transmitted back through the optical fiber or a separate optical fiber to a detector. The interference pattern is determined by and changes with the position of the reflective mirror which position is an indication of the pressure applied to the membrane over the cavity. Thus, the intensity of the returned light is an indication of the pressure of the liquid on the plate. Here again, the size of the pressure sensor is preferably smaller than one quarter of the size of the plate. Preferably the sensitivity of the sensor is smaller toward one end of the sensor plate. Again, the light producing circuits and light detection circuits are well known and are not described here.

FIGS. 12 and 13 show a slit rheometer of the invention with a rheometer body constructed of a bottom portion 120 and a top portion 121. The bottom portion 120 has at least two recessed sections, three recessed sections 122, 123, and 124 being shown, with varying depth h, FIG. 13, and fixed width. The recesses form a channel for liquid flow. The top portion 121 is a rheometer plate of the invention and includes an array of pressure sensors 125, FIG. 12, and indicated as wells 126 in FIG. 13, spaced in such a way that at least two sensors 125 are located to measure pressures at at least two different positions in each recessed section, 122, 123, and 124. Each recessed section is sufficiently long to ensure a fully developed flow inside of each section. The sensors are positioned to measure the pressure of the fully developed flow. The rheometer plate 121, as best seen in FIG. 13, has an opposite orientation to that shown in FIGS. 1–11. What has been referred to as the top wafer in earlier embodiments is wafer 121a orientated to form the bottom of the plate with the measuring surface facing downwardly into the liquid flow channel, and what has been referred to in earlier embodiments as the substrate is 121b oriented to form the top of the plate and top of the rheometer body. As is evident, the rheometer plate of the invention can be used in any orientation.

The preferred material for the bottom portion 120 is silicon, glasses, or other materials that are sufficiently rigid and are used in semiconductor or microelectromechanical processes and that can be processed with wet chemical etching, dry plasma etching, or hot embossing, or the combination of these. The bottom portion 120 can be also made of multiple layers if desired to form channels 122, 123, and 124. The width of the channel is significantly larger than the gap h of the channel in order to minimize the effect of the two sides of rectangular channels, and is preferably greater than ten times the gap at all channels 122, 123, and 124. The top portion 121 and the bottom portion 120 are constructed separately and then combined together with electrostatic bonding (anodic bonding) methods, low temperature glass bonding methods, eutectic bonding methods, or other methods depending on the materials or design.

FIGS. 14 and 15 show a slit rheometer constructed of a bottom portion 130 and a top portion 131. The bottom portion has at least two recessed sections, three recessed sections 132, 133, and 134 being shown, with varying width w and fixed depth. The recesses form a channel for liquid flow. The top portion 131 is a rheometer plate of the invention and includes an array of pressure sensors 135, FIG. 14, indicated as wells 136 in FIG. 15, spaced in such a way that at least two sensors 135 are located to measure pressures at at least two different positions in each recessed section 132, 133, and 134. Each section is sufficiently long to ensure a fully developed flow inside of each section. The sensors are positioned to measure the pressure of the fully developed flow. The channels are constructed in such a way that the width w to the gap ratio of each channel is sufficiently greater than ten in all channels.

With each of the slit rheometers shown, in use, a means to cause flow of liquid to be tested through the flow passage formed by the recesses in the slit rheometer is used to create liquid flow. Such means may be a pump or other source of pressurized liquid to be tested. During flow of liquid, the pressure exerted by the liquid at the locations of the pressure sensors is measured by each sensor and from such measurements the apparent viscosity and exact viscosity may be determined in known manner.

The orientation of the larger and smaller flow passages formed by the differently dimensioned recesses is shown as opposite in FIGS. 12 and 14. It will not make any difference which way the flow of liquid takes place through the slit or flow channel. The important flow property that is measured to determine apparent viscosity is the difference in pressure sensed by the two sensors in a particular dimensioned recess. Comparison of the measurements in differently dimensioned recesses is used to determine the exact viscosity of the liquid. While two differently dimensioned recesses will provide a reasonably accurate indication of exact viscosity, the more recesses present the better the accuracy. The presence of two or more recesses also allows the measurement of viscosity at multiple shear rates with one measurement. However, increased accuracy is offset by increased expense for more recesses. With the integrated recesses of the slit rheometers of the invention, the cost for increased recesses is reduced over the prior art where separate devices with different size slits were used, but there is still an increased cost for increased recesses. Excellent accuracy within the usually desired range can generally be obtained with two or three recesses.

While the described embodiments have been illustrated somewhat schematically with respect to the positioning and relative sizes of the various components on the top and bottom wafers, it should be realized that the various components and traces can be formed and positioned in any known manner or in any manner developed. Thus, various components or traces can be deposited on the surfaces of the wafers or can be embedded or buried in the wafers.

Whereas this invention is here illustrated and described with reference to embodiments thereof presently contemplated as the best mode of carrying out the invention in actual practice, it is to be realized that various changes may be made in adapting the invention to different embodiments without departing from the inventive concepts disclosed herein.

I claim:

1. A plate having a plurality of pressure sensors at spaced locations therein to measure pressure exerted against a substantially smooth measuring surface of the plate at the locations of the pressure sensors, comprising:

a plate having a substantially smooth measuring surface against which a liquid can act;

a plurality of cavities in the plate under the measuring surface;

deformable portions of the measuring surface of the plate extending over each of the plurality of cavities and resiliently deformable into the cavities in response to pressure applied to the deformable portions of the measuring surface; and a single sensor in each of the plurality of cavities, each sensor cooperable with the deformable portion of the measuring surface extending over that cavity to sense the deformation of such deformable portion and provide a signal indicative of a single deformation sensed, the deformation of the deformable portions being indicative of the pressure applied to such deformable portions.

2. A plate having a plurality of pressure sensors according to claim 1, wherein the measuring surface is formed by a wafer secured to a substrate.

3. A plate having a plurality of pressure sensors according to claim 2, wherein the cavities are created by wells formed in the wafer, the wells resulting in thin portions of the wafer that extend over the wells and form the deformable portions of the measuring surface.

4. A plate having a plurality of pressure sensors according to claim 2, wherein the cavities are created by wells formed in the substrate, wherein portions of the wafer extend over the wells in the substrate, the portions of the wafer which extend over the wells forming the deformable portions of the measuring surface.

5. A plate having a plurality of pressure sensors according to claim 2, additionally including a spacer positioned between the wafer and the substrate, wherein the cavities are created by openings extending through the spacer, wherein portions of the wafer extend over the openings in the spacer, the portions of the wafer which extend over the openings in the spacer forming the deformable portions of the measuring surface.

6. A plate having a plurality of pressure sensors according to claim 2, wherein a deformable portion of the measuring surface forms a side of each cavity and the substrate forms an opposite side of each cavity, and wherein the sensors are capacitive sensors formed by a capacitor plate on the deformable portion of the measuring surface in each cavity and a capacitor plate on the substrate on the opposite side of the each cavity.

7. A plate having a plurality of pressure sensors according to claim 6, wherein the capacitor plates are formed by conductive layers deposited on the opposite sides of the cavities.

8. A plate having a plurality of pressure sensors according to claim 7, additionally including conductive leads extending from each capacitor plate to a contact pad for connection to a sensor circuit.

9. A plate having a plurality of pressure sensors according to claim 2, wherein a deformable portion of the measuring surface forms a side of each cavity and the substrate forms an opposite side of each cavity, and wherein the sensors are optical sensors formed by a reflective mirror on the deformable portion of the measuring surface in each cavity, a partially transparent layer on the substrate on the opposite side of each cavity, a light source to direct light to the partially transparent layer so a portion of the light is passed through the partially transparent layer to the reflecting mirror and a portion of the light is reflected back from the partially transparent layer, whereby at least a portion of the light passed to the reflective mirror is reflected back through the partially transparent layer and interacts with the light reflected from the partially transparent layer to create an interference pattern, and a sensor to sense the intensity of the light at a fixed location in the interference pattern, the intensity of the light sensed being an indication of the deformation of the deformable portion.

10. A plate having a plurality of pressure sensors according to claim 1, additionally including a protective layer on the measuring surface.

11. A plate having a plurality of pressure sensors according to claim 1, additionally including an air passage connecting each cavity with the atmosphere.

12. A plate having a plurality of pressure sensors according to claim 1, additionally including a proximity sensor in the plate to measure the distance of a sensed object from the measuring surface.

13. A plate having a plurality of pressure sensors according to claim 12, wherein the proximity sensor is a capacitive sensor.

14. A plate having a plurality of pressure sensors according to claim 1, wherein the length of each deformable portion is less than one-quarter of the length of the plate.

15. A plate having a plurality of pressure sensors according to claim 1, wherein different sensors of the plurality of sensors vary in their measurement sensitivity.

16. A plate having a plurality of pressure sensors according to claim 1, wherein the plate forms one side of a flow passage through a body having a plurality of recesses, each recess of the plurality of recesses in the body having different dimensions and being connected together in series to form the flow passage through the body;

means for causing flow of fluid through the recesses; and wherein a plurality of the plurality of pressure sensors are associated with each recess to provide indications of pressure exerted by fluid in the recess against the recess at the location of each of the pressure sensors associated with the recess to thereby form a slit rheometer.

17. A plate having a plurality of pressure sensors according to claim 16, wherein there are at least two recesses.

18. A plate having a plurality of pressure sensors according to claim 16, wherein there are at least two pressure sensors associated with each recess.

19. A plate having a plurality of pressure sensors according to claim 1, additionally including at least one temperature sensor to sense the temperature of the measuring surface of the plate.

20. A plate having a plurality of pressure sensors according to claim 1, additionally including a plurality of temperature sensors to sense the temperature of the measuring surface of the plate at the location of the temperature sensors.

21. A pressure sensor, comprising:

a wafer having opposite sides, one side forming a smooth measuring surface against which a liquid may exert pressure;

a plurality of wells extending into the wafer from the side opposite the measuring side, said wells forming thin deformable portions of the wafer between ends of individual wells and the smooth measuring surface, said thin deformable portions deformable with respect to an individual well in response to pressure applied to the smooth measuring surface over said individual well; and detectors associated with individual wells of the plurality of wells to detect the deformation of the thin portion of the wafer with respect to individual wells and to provide an output indicative of the pressure applied to that thin section.

22. A pressure sensor according to claim 21, additionally including a substrate mounted on the side of the wafer opposite the measuring side and extending over the plurality of wells, and wherein the detectors for the wells include an electrically conductive material on the thin sections within the wells and electrically conductive material within the wells on the substrate extending over the wells, the electrically conductive material within the wells forming capacitors whose capacitance varies with the deformation of the thin sections.

23. A pressure sensor according to claim 21, wherein the wafer is made up of a spacer having a plurality of openings extending therethrough, and a thin wafer joined to the spacer and extending over the openings therethrough, said thin wafer forming the smooth measuring surface and the thin portions where the wafer extends over an opening in the spacer, and the openings in the spacer forming the wells.

24. A pressure sensor, comprising:

a substrate;

a plurality of wells extending into the substrate from a joining surface of the substrate;

a wafer having opposite sides, one side forming a smooth measuring surface against which a liquid may exert pressure and an opposite side joined to the joining side of the substrate, the wafer forming thin deformable portions of the wafer where the wafer extends over a well, said thin deformable portions deformable with respect to an individual well in response to pressure applied to the smooth measuring surface over said individual well; and detectors associated with individual wells of the plurality of wells to detect the deformation of the thin portion of the wafer with respect to individual wells and to provide an output indicative of the pressure applied to that thin section.

25. A pressure sensor according to claim 24, wherein the detectors for the wells include an electrically conductive material within the wells on the thin sections extending over the wells, and electrically conductive material within the wells on the substrate, the electrically conductive material within the wells forming capacitors whose capacitance varies with the deformation of the thin sections.

26. A method of producing a plate with a plurality of pressure sensors, comprising the steps of:

obtaining a wafer and a substrate;

forming a plurality of wells in one of the wafer or the substrate;

forming sensor components in the wells;

joining the wafer and substrate to form the plate in a manner so that the wells form cavities in the plate with thin deformable portions of the wafer forming a part of each cavity, the thin deformable portions of the wafer deforming with respect to the cavities in response to liquid pressure applied to the plate, and the sensor components being arranged in the wells to measure the deformation of respective thin sections.

* * * * *